US012710371B2

(12) United States Patent
Lant et al.

(10) Patent No.: US 12,710,371 B2
(45) Date of Patent: Aug. 18, 2026

(54) METHODS FOR MAKING CLEANING COMPOSITIONS AND DETECTING SOILS

(71) Applicant: The Procter & Gamble Company, Cincinnati, OH (US)

(72) Inventors: Neil Joseph Lant, Newcastle Upon Tyne (GB); Nazarmohammad Gulamhussain Momin, Newcastle Upon Tyne (GB); Ana Morales Garcia, Newcastle Upon Tyne (GB); Catherine Jones, Stocksfield (GB); William G. T Willats, Newcastle Upon Tyne (GB); Hamish Chun Lam Yau, Newcastle Upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 921 days.

(21) Appl. No.: 17/736,130

(22) Filed: May 4, 2022

(65) Prior Publication Data

US 2022/0373467 A1 Nov. 24, 2022

(30) Foreign Application Priority Data

May 5, 2021 (EP) .................................... 21172342

(51) Int. Cl.
*G01N 21/78* (2006.01)
*C11D 3/00* (2006.01)
*G01N 33/52* (2006.01)

(52) U.S. Cl.
CPC ........... *G01N 21/78* (2013.01); *C11D 3/0005* (2013.01); *G01N 33/52* (2013.01)

(58) Field of Classification Search
CPC .... G01N 21/78; G01N 33/52; G01N 33/5308; G01N 33/566; C11D 3/0005; C11D 2111/44; C11D 3/38636; C11D 3/386
See application file for complete search history.

(56) References Cited

U.S. PATENT DOCUMENTS

| | | | |
|---|---|---|---|
| 6,613,505 | B2 | 9/2003 | Shih |
| 8,945,860 | B2 | 2/2015 | Yang et al. |
| 12,105,108 | B2 | 10/2024 | Dimov et al. |

(Continued)

FOREIGN PATENT DOCUMENTS

| | | | |
|---|---|---|---|
| WO | 9933946 | A1 | 7/1999 |
| WO | 0196018 | A2 | 12/2001 |

OTHER PUBLICATIONS

Liu, "Developing novel enzymes for laundry industry", Thesis, Dec. 2010, Institute of Cell and Molecular Biosciences, Newcastle, pp. 1-285. (Year: 2010).*

(Continued)

*Primary Examiner* — Dennis White
(74) *Attorney, Agent, or Firm* — Abigail O. Idokogi; Carrie Schwartz

(57) ABSTRACT

A method of identifying a residue-component in a residue on a surface includes using molecular probes. The molecular probes may be antibodies, affimers, aptamers, lectins, carbohydrate binding modules and mixtures thereof. The residue-component may be a soil or surface treatment component. The method can be used to make or improve cleaning or treatment compositions or processes.

20 Claims, 1 Drawing Sheet

Molecular probe specificity
Algal cell wall polysaccharides
Alginates
Callose
DNA
Mannan
Pectic polysaccharides
Plasma membrane glycoproteins
Proteoglycans
Xylans
Xyloglucans
Controls
Repeat 1
Repeat 2
Repeat 3
A, Soiled stain; B, Unsoiled cotton.
Relative abundance (%)

(56) References Cited

U.S. PATENT DOCUMENTS

2019/0264139 A1 8/2019 Lant et al.

OTHER PUBLICATIONS

CM05328F Extended European Search Report and Search Opinion; Application No. 21172342.4; dated Nov. 29, 2021; 09 pages.
CM05328M Extended European Search Report and Search Opinion; Application No. 22171554.3; dated Oct. 27, 2022; 09 pages.
CM05328M PCT Search Report and Written Opinion for PCT/US2022/027561 dated Aug. 29, 2022, 13 pages.
Morales-Garcia A.L. et al. : "The application of a nuclease enzyme toclean stubborn soils and odors in laundry", J. Surfact. Deterg., vol. 23,No. 4, Feb. 19, 2020, pp. 797-807.
Vidal-Melgosa S. et al. : "A new versatile microarray-based method forhigh throughput screening of carbohydrate-active enzymes", J. Biol.Chem., vol. 290, No. 14, Apr. 3, 2015, pp. 9020-9036.
Yau H.C. L. et al.: "Removal of eDNA from fabrics using a novel laundry DNase revealed using high-resolution imaging", Scientific Reports, vol. 11, 21542, Nov. 2, 2021, pp. 1-10,XP55858429.
Hiromitsu Takaoka et al. "Odorous components for clothes after being dried indoor and odor-reducing effect of detergent", Fragrance Journal, vol. 30, No. 7, Jul. 15, 2002, pp. 79-83.
Hiroyuki Hnihara et al. "Detergents deodorizing odors from cloths ager being dried indoor", Kaori no hon (Book of Smell), No. 223, Sep. 2004, pp. 109-116.

* cited by examiner

| Molecular probe specificity | | | Algal cell wall polysaccharides | | | | Alginates | | | | | | Callose | DNA | | | Mannan | | | | Pectic polysaccharides | | | | | | | | | | | | | Plasma membrane glycoproteins | Proteoglycans | | | | | | | | | | | | | | Xylans | | | | Xyloglucans | | | Controls | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Repeat 1 | H2O | A | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | | B | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | CDTA | A | 1 | 1 | 1 | 1 | 0 | 0 | 8 | 1 | 2 | 1 | 0 | 0 | 0 | 1 | 4 | 0 | 14 | 28 | 0 | 2 | 0 | 0 | 0 | 1 | 0 | 0 | 1 | 0 | 1 | 1 | 1 | 1 | 0 | 0 | 1 | 1 | 0 | 1 | 1 | 0 | 0 | 1 | 2 | 0 | 0 | 1 | 0 | 1 | 0 | 1 | 0 | 0 | 1 | 0 | 0 | 1 |
| | | B | 0 | 1 | 0 | 2 | 1 | 2 | 3 | 1 | 1 | 0 | 1 | 0 | 0 | 0 | 0 | 0 | 2 | 1 | 2 | 2 | 0 | 0 | 1 | 0 | 0 | 0 | 1 | 1 | 0 | 1 | 1 | 4 | 1 | 0 | 0 | 1 | 0 | 1 | 1 | 0 | 0 | 2 | 0 | 0 | 3 | 1 | 1 | 1 | 0 | 1 | 0 | 1 | 2 | 0 | 1 | 1 |
| | NaOH | A | 2 | 1 | 1 | 1 | 1 | 1 | 2 | 1 | 2 | 1 | 3 | 3 | 0 | 1 | 22 | 1 | 47 | 100 | 0 | 1 | 0 | 0 | 1 | 1 | 3 | 1 | 1 | 0 | 7 | 1 | 1 | 2 | 2 | 3 | 1 | 2 | 1 | 2 | 1 | 1 | 0 | 6 | 1 | 1 | 1 | 1 | 7 | 1 | 1 | 2 | 6 | 1 | 7 | 1 | 1 | 1 |
| | | B | 1 | 1 | 0 | 1 | 1 | 2 | 2 | 0 | 2 | 2 | 2 | 6 | 0 | 1 | 3 | 2 | 1 | 14 | 1 | 1 | 1 | 1 | 1 | 12 | 0 | 1 | 1 | 1 | 1 | 2 | 1 | 1 | 2 | 2 | 1 | 1 | 5 | 1 | 1 | 2 | 0 | 6 | 37 | 1 | 1 | 0 | 0 | 1 | 2 | 3 | 15 | 1 | 23 | 1 | 1 | 1 |
| | NaCl | A | 21 | 2 | 0 | 7 | 0 | 2 | 1 | 0 | 1 | 2 | 0 | 8 | 0 | 0 | 3 | 1 | 23 | 7 | 0 | 0 | 0 | 3 | 1 | 1 | 5 | 1 | 1 | 1 | 0 | 1 | 1 | 1 | 1 | 1 | 1 | 1 | 2 | 2 | 0 | 0 | 1 | 1 | 1 | 0 | 1 | 0 | 1 | 0 | 0 | 1 | 1 | 3 | 3 | 0 | 0 | 1 |
| | | B | 2 | 4 | 0 | 1 | 0 | 1 | 1 | 1 | 0 | 0 | 1 | 1 | 0 | 1 | 0 | 1 | 2 | 2 | 0 | 0 | 1 | 5 | 1 | 1 | 1 | 1 | 1 | 1 | 1 | 1 | 1 | 1 | 14 | 1 | 1 | 1 | 0 | 1 | 0 | 1 | 1 | 1 | 2 | 0 | 0 | 0 | 0 | 2 | 0 | 2 | 6 | 2 | 21 | 1 | 0 | 1 |
| Repeat 2 | H2O | A | 0 | 0 | 1 | 0 | 0 | 0 | 0 | 0 | 1 | 0 | 0 | 1 | 0 | 0 | 7 | 0 | 8 | 13 | 2 | 0 | 0 | 0 | 0 | 0 | 0 | 1 | 0 | 1 | 1 | 0 | 1 | 0 | 0 | 1 | 1 | 0 | 1 | 1 | 0 | 0 | 0 | 1 | 0 | 0 | 0 | 0 | 0 | 1 | 0 | 0 | 0 | 0 | 0 | 0 | 0 | 0 |
| | | B | 0 | 3 | 1 | 1 | 0 | 1 | 0 | 0 | 0 | 0 | 1 | 0 | 0 | 1 | 0 | 0 | 0 | 1 | 0 | 0 | 0 | 0 | 0 | 0 | 0 | 2 | 5 | 1 | 0 | 0 | 1 | 0 | 0 | 0 | 1 | 0 | 0 | 0 | 0 | 1 | 0 | 1 | 0 | 0 | 0 | 0 | 0 | 0 | 0 | 0 | 0 | 0 | 1 | 0 | 1 | 1 |
| | CDTA | A | 0 | 0 | 0 | 1 | 1 | 0 | 0 | 0 | 0 | 0 | 0 | 1 | 0 | 0 | 2 | 0 | 6 | 14 | 0 | 0 | 1 | 0 | 0 | 0 | 0 | 0 | 0 | 0 | 0 | 0 | 0 | 0 | 0 | 0 | 1 | 0 | 0 | 1 | 0 | 0 | 0 | 0 | 0 | 0 | 0 | 0 | 0 | 4 | 0 | 0 | 0 | 0 | 1 | 0 | 0 | 0 |
| | | B | 0 | 0 | 0 | 1 | 1 | 0 | 0 | 0 | 0 | 0 | 1 | 0 | 0 | 1 | 0 | 0 | 0 | 1 | 0 | 0 | 0 | 0 | 0 | 0 | 0 | 1 | 0 | 0 | 0 | 0 | 1 | 0 | 0 | 0 | 0 | 0 | 0 | 1 | 0 | 0 | 0 | 0 | 0 | 0 | 1 | 0 | 1 | 1 | 0 | 0 | 0 | 0 | 3 | 0 | 0 | 0 |
| | NaOH | A | 1 | 0 | 1 | 1 | 4 | 1 | 0 | 0 | 0 | 1 | 1 | 0 | 0 | 0 | 17 | 0 | 51 | 72 | 0 | 0 | 0 | 0 | 0 | 1 | 0 | 1 | 3 | 1 | 0 | 0 | 1 | 0 | 1 | 0 | 0 | 1 | 1 | 1 | 0 | 1 | 1 | 0 | 0 | 0 | 0 | 1 | 0 | 1 | 0 | 1 | 1 | 0 | 2 | 1 | 1 | 0 |
| | | B | 0 | 0 | 1 | 2 | 0 | 0 | 0 | 1 | 0 | 0 | 1 | 0 | 0 | 1 | 2 | 0 | 2 | 14 | 1 | 0 | 0 | 0 | 0 | 1 | 1 | 0 | 0 | 1 | 1 | 0 | 1 | 0 | 0 | 0 | 1 | 1 | 1 | 1 | 1 | 0 | 1 | 0 | 1 | 0 | 0 | 0 | 1 | 1 | 0 | 1 | 3 | 2 | 12 | 0 | 0 | 0 |
| | NaCl | A | 0 | 0 | 1 | 0 | 0 | 0 | 0 | 0 | 0 | 0 | 1 | 0 | 0 | 0 | 5 | 0 | 17 | 59 | 0 | 1 | 0 | 1 | 0 | 0 | 2 | 0 | 1 | 0 | 1 | 0 | 0 | 0 | 0 | 0 | 0 | 0 | 0 | 0 | 0 | 0 | 0 | 0 | 0 | 0 | 0 | 0 | 0 | 1 | 0 | 1 | 0 | 1 | 1 | 0 | 0 | 0 |
| | | B | 0 | 0 | 0 | 1 | 0 | 1 | 0 | 1 | 1 | 0 | 0 | 0 | 0 | 1 | 0 | 0 | 0 | 1 | 3 | 1 | 0 | 0 | 0 | 0 | 0 | 0 | 0 | 0 | 0 | 0 | 1 | 0 | 1 | 1 | 1 | 0 | 0 | 0 | 1 | 1 | 3 | 0 | 0 | 2 | 1 | 0 | 1 | 0 | 0 | 0 | 1 | 1 | 1 | 0 | 0 | 0 |
| Repeat 3 | H2O | A | 1 | 0 | 0 | 1 | 0 | 2 | 0 | 0 | 0 | 0 | 0 | 0 | 0 | 0 | 0 | 0 | 3 | 14 | 0 | 1 | 0 | 0 | 0 | 0 | 1 | 1 | 0 | 2 | 0 | 0 | 0 | 0 | 0 | 0 | 0 | 4 | 0 | 0 | 0 | 0 | 0 | 0 | 1 | 0 | 0 | 1 | 0 | 4 | 0 | 0 | 0 | 0 | 0 | 0 | 1 | 1 |
| | | B | 0 | 0 | 0 | 0 | 0 | 3 | 1 | 0 | 0 | 0 | 1 | 0 | 0 | 1 | 0 | 0 | 0 | 0 | 0 | 0 | 0 | 0 | 1 | 0 | 0 | 1 | 0 | 1 | 2 | 0 | 0 | 0 | 0 | 0 | 0 | 0 | 0 | 1 | 0 | 0 | 0 | 0 | 0 | 0 | 0 | 4 | 2 | 0 | 0 | 0 | 0 | 0 | 0 | 1 | 1 | 0 |
| | CDTA | A | 1 | 0 | 0 | 0 | 0 | 0 | 0 | 0 | 0 | 0 | 0 | 0 | 0 | 0 | 5 | 0 | 1 | 23 | 0 | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 0 | 0 |
| | | B | 0 | 0 | 0 | 0 | 0 | 0 | 0 | 0 | 0 | 0 | 0 | 0 | 0 | 0 | 2 | 0 | 0 | 8 | 0 | 0 | 0 | 0 | 0 | 0 | 0 | 0 | 0 | 1 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 |
| | NaOH | A | 0 | 0 | 0 | 1 | 0 | 0 | 0 | 0 | 0 | 0 | 1 | 0 | 0 | 0 | 26 | 1 | 16 | 41 | 0 | 0 | 0 | 0 | 0 | 0 | 0 | 0 | 1 | 1 | 0 | 1 | 0 | 0 | 0 | 0 | 0 | 0 | 0 | 0 | 0 | 0 | 0 | 0 | 0 | 0 | 0 | 0 | 0 | 3 | 0 | 0 | 5 | 0 | 19 | 0 | 0 | 0 |
| | | B | 0 | 0 | 0 | 0 | 0 | 0 | 0 | 0 | 0 | 0 | 1 | 0 | 0 | 0 | 12 | 1 | 4 | 35 | 0 | 0 | 0 | 0 | 0 | 0 | 0 | 0 | 0 | 2 | 0 | 1 | 0 | 0 | 0 | 0 | 0 | 0 | 0 | 0 | 0 | 1 | 0 | 0 | 0 | 0 | 0 | 0 | 0 | 1 | 0 | 1 | 10 | 1 | 27 | 0 | 0 | 0 |
| | NaCl | A | 0 | 0 | 0 | 0 | 0 | 0 | 0 | 0 | 0 | 0 | 1 | 0 | 0 | 0 | 21 | 1 | 14 | 26 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 3 | 0 | 0 | 0 |
| | | B | 0 | 0 | 0 | 0 | 0 | 0 | 0 | 0 | 0 | 0 | 0 | 0 | 0 | 0 | 1 | 0 | 6 | 14 | 1 | 0 | 0 | 0 | 0 | 0 | 0 | 0 | 1 | 1 | 0 | 0 | 0 | 0 | 0 | 0 | 0 | 0 | 0 | 0 | 0 | 0 | 0 | 0 | 1 | 0 | 0 | 0 | 0 | 1 | 0 | 0 | 3 | 0 | 16 | 0 | 0 | 0 |

A, Soiled stain; B. Unsoiled cotton.

Relative abundance (%)

METHODS FOR MAKING CLEANING COMPOSITIONS AND DETECTING SOILS

FIELD OF THE INVENTION

The present invention relates to a method of determining a component in a residue on a surface, particularly on fabric or hard surfaces. The residue may be a soil on the surface or may be a surface treatment composition deposited on a surface or mixture thereof. The residue is typically a complex, multi-component residue. The invention also relates to a method of making a cleaning and/or treatment composition and a method of using a cleaning and/or treatment composition, and a method for determining the efficacy of a cleaning and/or treatment process and/or composition and/or component thereof.

BACKGROUND OF THE INVENTION

In cleaning and treatment applications it is a constant challenge to provide improved efficacy. The challenge is compounded by increased desire to provide effective cleaning processes and compositions which are also environmentally responsible in terms of use of chemistry, increased use of low washing temperatures (e.g., cold water), shorter washing times and lower wash water volumes, which may all contribute to reduced efficacy.

Thus, it is an object of the present invention to enable preparation of cleaning and treatment compositions to maximise efficacy, with targeted performance against today's cleaning and treatment challenges. The present inventors have found that by improved understanding of residues on surfaces these challenges can be addressed. However, surface residues may be extremely complex and particularly over time, on aging, chemical reactions take place changing the nature of the residue and increasing its complexity. Traditional analytical tools may require separation of components and/or may be unable to differentiate between different components in the residue, particularly in a complex mixture and particularly where the residue comprises multiple polymeric components. There is therefore still a need for characterization of surface residues comprising complex mixtures, particularly those comprising multiple polymeric components, to enable effective cleaning and treatment compositions and processes to be developed.

BRIEF DESCRIPTION OF THE DRAWING

FIG. 1. shows a heatmap reflecting the relative abundance of soil residues identified in the samples of interest (soiled and unsoiled cotton) revealed through molecular probe analysis following sequential extraction steps with i) water; ii) 50 mM Cyclohexane-Diamine-Tetra-Acetic acid (CDTA) pH 7.5; iii) 4 M Sodium hydroxide (NaOH), 0.1% (w/v) Sodium borohydride ($NaBH_4$); iv) 3M Sodium Chloride (NaCl); carried out at ambient room temperature.

SUMMARY OF THE INVENTION

The invention provides a method of identifying a residue and/or residue-component in a residue on a surface, comprising (i) in a first step, contacting the residue with at least three molecular probes selected from the group comprising antibodies, affimers, aptamers, lectins, carbohydrate binding modules and mixtures thereof; (ii) in a second step, detecting a positive response from one or more probes, the collective response from said at least three molecular probes providing information regarding the identity, and optionally quantity, of the residue and/or residue-component in the residue. The residue may comprise soil.

The invention also provides a method of making a cleaning composition comprising (i) in a first step, contacting a residue and/or residue component in a residue on a surface with at least three molecular probes selected from the group comprising antibodies, affimers, aptamers, lectins, carbohydrate binding modules and mixtures thereof; (ii) in a second step, detecting a positive response from one or more probes, the collective response from said at least three molecular probes providing information regarding the identity of the residue and/or residue-component in the residue, to provide an identified residue and/or identified residue-component; and (iii) selecting a first cleaning component capable of promoting removal of the identified residue and/or identified residue-component, and (iv) mixing the first cleaning component with a cleaning adjunct to form a cleaning composition.

The identified residue or residue-component is preferably a substrate for an enzyme and the first cleaning component comprises an enzyme or enzyme-precursor for said substrate.

The invention also provides a method of determining relative performance, and optionally improving a cleaning process or cleaning composition, comprising (i) cleaning a soiled surface in a first cleaning process, said first cleaning process having one or more cleaning conditions selected from the list comprising: wash time, temperature, number or sequence of wash steps, wash water volume and/or other physical conditions and/or cleaning composition and/or concentration thereof, and/or order of addition of cleaning composition components in pre-wash, wash and/or rinse steps, to provide a cleaned surface; (ii) identifying a residue and/or residue-component remaining on the cleaned surface as above, (iii) optionally quantifying such residue and/or residue component; (iv) changing one or more cleaning conditions, to provide a second cleaning process; (v) cleaning the soiled surface in said second cleaning process (vi) identifying the residue and/or residue-component remaining on the cleaned surface as above; (vii) optionally quantifying such residue and/or residue component after said second cleaning process; (viii) comparing the residue and/or residue component and optionally quantity thereof, remaining after the first cleaning process and after the second cleaning process to determine the relative performance of the first cleaning process and/or cleaning composition used therein, and the second cleaning process and/or cleaning composition used therein, thus enabling determination of the most effective cleaning process.

The invention also provides a method of determining relative performance or improving a surface treatment composition and/or process comprising depositing a surface treatment component onto a surface, the method comprising (i) treating a surface in a first surface treatment process having one or more treatment conditions selected from: temperature, number or sequence of treatment steps, number or sequence of wash and/or rinse steps, wash and/or rinse water volume and/or other physical conditions, and/or surface treatment composition and concentration thereof, and/or surface treatment component order of addition in pre-wash, wash and/or rinse steps, (ii) identifying and/or quantifying a residue and/or residue-component which is a surface treatment component remaining on the surface, as described above, (iii) changing at least one of the treatment conditions to provide a second surface treatment process, (iv) treating the surface with the second treatment process, (v) identifying and/or quantifying the residue and/or residue-component after the second surface treatment process, (vi) comparing the residue and/or residue component and optionally quantity thereof, remaining after the first treatment process and after the second treatment process to determine the relative performance of the first treatment process and the second treatment process.

The methods of the invention may comprise the additional step of quantifying the residue and/or residue-component. Preferably the molecular probes comprise molecular probes providing a colorimetric response on binding. Preferably the surface, especially the support surface is in the form of a micro-array.

Thus, the invention provides a method of identifying a residue and/or residue-component in a residue on a surface, comprising (i) in a first step, contacting the residue with at least three molecular probes selected from the group comprising antibodies, affimers, aptamers, lectins, carbohydrate binding modules and mixtures thereof; (ii) in a second step, detecting a positive response from one or more probes, the collective response from said at least three molecular probes providing information regarding the identity of the residue and/or residue-component in the residue. The present invention may also be used to compare different residue and/or residue components on surfaces for example following different soiling and/or treatment and/or aging steps.

The residue may be contacted with the three or more molecular probes in situ on the surface. Alternatively, the residue is extracted from the surface in a residue extraction step, prior to contacting the at least three molecular probes.

The invention is particularly useful for identifying/characterizing a residue and/or residue-component in a complex soil residue, preferably comprising more than one polymeric residue-component. In particular the invention provides a method for characterizing a residue and/or residue-component without the need for separation of the residue-components.

The invention is also particularly useful for identifying/characterizing a residue component which is present at relatively low levels in the residue, for example in an amount below 10 wt % or below 5 wt % or below 2 wt % or below 1 wt % or even below 0.5 wt % based on the total weight percent of the residue. This is useful because certain residue components, particularly polymeric components can be strongly implicated in adhering soil residues in spite of being present in a residue at low levels.

The invention includes providing a method of making a cleaning composition comprising (1) identifying a residue and/or residue-component in a residue on a surface, comprising (i) in a first step, contacting the residue with at least three molecular probes selected from the group comprising antibodies, affimers, aptamers, lectins, carbohydrate binding modules and mixtures thereof; (ii) in a second step, detecting a positive response from one or more probes, the collective response from said at least three molecular probes providing information regarding the identity of the residue and/or residue-component in the residue, and (2) based on the information provided by the response, selecting a first cleaning component capable of promoting removal of the residue and/or residue-component, and (3) mixing the first cleaning component with a cleaning adjunct to form a cleaning composition.

In a preferred method for making a cleaning composition, the method comprises (1) washing a soiled surface with an aqueous wash liquor, optionally comprising a cleaning composition or component thereof, to partially remove the soil residue from the surface, and optionally drying the surface, (2) identifying a residue and/or residue-component in the remaining soil on the surface by: (i) in a first step, contacting the residue with at least three molecular probes selected from the group comprising antibodies, affimers, aptamers, lectins, carbohydrate binding modules and mixtures thereof; (ii) in a second step, detecting a positive response from one or more probes, the collective response from said at least three molecular probes providing information regarding the identity of the residue and/or residue-component in the residue, (3) based on the information provided by the response, selecting a first cleaning component capable of promoting removal of the residue-component, and (4) mixing the first cleaning component with a cleaning adjunct to form a cleaning composition.

The invention also includes providing a method of determining relative performance of a cleaning component, composition or process, comprising (i) in a first cleaning process, cleaning a soiled surface in a cleaning process optionally in the presence of a cleaning or treatment composition or component, to provide a cleaned surface; (ii) identifying and/or quantifying a residue and/or residue-component remaining on the cleaned surface as described above, (iii) changing the wash time, temperature, number or sequence of wash steps, wash water volume and/or other physical conditions and/or cleaning composition and/or cleaning component and/or step or order of addition of cleaning composition and/or components in pre-wash, wash and/or rinse steps, to provide a second cleaning process (iv) cleaning the soiled surface in the second cleaning process (v) identifying and/or quantifying the residue and/or residue-component after the second cleaning process, and (vi) comparing the degree of reduction in the residue and/or one or more residue-components between the first and second wash processes to determine the relative performance of the process or cleaning composition or cleaning component.

The invention includes providing a method for improving a cleaning process, cleaning composition and/or cleaning component by carrying out these steps, and selecting the process, composition and/or component which produces the greatest removal of the residue and/or removal of one or more residue-components.

The invention includes providing a method of determining relative performance or improving a surface treatment composition, component and/or process comprising depositing a surface treatment composition or component onto a surface, the method comprising (i) treating a surface with a surface treatment process, component or composition in a first treatment process, (ii) identifying and/or quantifying a residue and/or residue-component which is a surface treatment component remaining on the surface, using molecular probes as described above, (iii) changing the temperature, number or sequence of wash, rinse and/or treatment steps, wash or rinse water volume and/or other physical conditions and/or surface treatment composition and/or surface treatment component and/or order of addition in pre-wash, wash and/or rinse steps, to provide a second surface treatment process (iv) treating the surface according to the second surface treatment process (iv) identifying and/or quantifying the residue and/or residue-component after the second surface treatment process and (vi) comparing the residue and/or one or more residue-components between the first and second processes to determine the relative performance of the surface treatment process steps and/or compositions or surface treatment components.

The invention includes providing a method for improving a surface treatment process, composition and/or component by carrying out these steps, and selecting the process, composition and/or component which produces the most effective surface treatment.

The method of the invention may be carried out by identifying a residue and/or residue-component in a residue on a surface, comprising (i) extracting the residue from the surface in an extraction step, (ii) immobilising the extracted residue on a support surface, (iii) contacting the extracted residue with at least two molecular probes selected from the group comprising antibodies, affimers, aptamers, lectins, carbohydrate binding modules and mixtures thereof; (iv) detecting a positive response from one or more probes, said response providing information regarding the identity of the residue-component in the residue.

Preferably the residue comprises soil. Preferably the surface comprises a fabric surface, hard surface, or a surface of skin, teeth or hair, preferably a fabric surface or hard surface. Preferably the residue is extracted from the surface in a residue removal step, prior to step (i).

The method of making a cleaning composition may comprise (1) identifying a residue and/or residue-component in a soil on a surface by: (i) extracting the soil from the surface in an extraction step, (ii) immobilising the extracted soil on a support surface, (iii) contacting the extracted soil with at least two molecular probes selected from the group comprising antibodies, affimers, aptamers, lectins, carbohydrate binding modules and mixtures thereof, (iv) detecting a positive response from one or more probes, said response providing information regarding the identity of the residue and/or residue-component in the soil; (2) based on the information provided by the response selecting a first cleaning component capable of promoting removal of the residue and/or residue-component, then (3) mixing the first cleaning component with a cleaning adjunct to form a cleaning composition.

In a preferred method for making a cleaning composition, the method comprises (1) washing a soiled surface with an aqueous wash liquor, optionally comprising a cleaning composition or component to partially remove the soil residue from the surface, and optionally drying the surface, (2) identifying a residue and/or residue-component in the remaining soil on the surface by: (i) extracting the remaining soil from the surface in an extraction step to obtain extracted soil, (ii) immobilising the extracted soil on a support surface, (iii) contacting the extracted soil with at least two molecular probes selected from the group comprising antibodies, affimers, aptamers, lectins, carbohydrate binding modules and mixtures thereof, (iv) detecting a positive response from one or more probes, said response providing information regarding the identity of a residue and/or residue-component in the remaining soil; (3) based on the information provided by the response selecting a first cleaning component capable of promoting removal of the residue and/or residue-component, then (4) mixing the first cleaning component with a cleaning adjunct to form a cleaning composition.

The methods of the invention may also be used to quantify the residue and/or one or more residue-components. The quantitative information may be absolute or relative. The invention may also be used to determine the efficacy of a surface cleaning or treatment process, composition and/or component.

DETAILED DESCRIPTION OF THE INVENTION

The surface residue is typically a complex mixture. It may comprise for example, soil on a soiled surface, and/or a surface-deposited composition or component thereof which has been deposited in a prior treatment step to confer a benefit on the surface. In particular, the surface residue comprises a complex soil on a soiled surface.

The surface may be for example a fabric surface, hard surface, or a surface of skin, teeth or hair, preferably fabric or hard surfaces, particularly fabric surfaces. Any fabric surface is suitable, for example, fabrics comprising natural fabrics such as cotton or cellulose (including paper), silk, wool or synthetic or mixed fabrics, such as nylon, polyester, poly-cotton or polyurethane such as Lycra™. By hard surfaces is intended surfaces for cleaning in the home such as floors, walls, surfaces in bathrooms and kitchens such as tiled surfaces and counters, and in particular dish-washing. Thus, the invention is particularly useful for addressing the challenge of removing a complex soil which may comprise for example, bodily secretions such as sebum, and/or incidental stains such as foods, and particulate soils arising from use, and/or treatment. Such soils are difficult to remove and in particular aged soils can be especially challenging because over time components in the soil can undergo chemical reactions such as oxidation, hydrolysis, polymerisation and condensation which increase the presence of complex components including polymers which tend to adhere the soils more firmly to the surface.

The molecular probes are molecules which have an affinity to a specific substrate or epitope of a polymer or other component in the residue including non-polymeric components. Whether a specific probe binds or not, and optionally also the degree of binding of a specific probe provides specific information about the presence of certain chemical moieties or bonds within the residue, the collective response of the probes revealing information about the identity of a residue and/or residue-component(s) within a residue. As used herein, "identifying" or "characterizing" (used interchangeably herein) means providing information regarding the identity of a residue or residue-component, for example relating to the chemistry, i.e. chemical moieties or bonds within the residue component. This information may provide an indication of the chemical type/class of a residue component, or the configuration/structure or motif of a residue component in the residue and the amount or relative amount of such chemical moieties, bonds and/or class, configuration/structure and/or motifs. The collective binding patterns are referred to as profiles and they are distinct for a given residue/soil comprising one or more residue-component/soil-components. The collective response of the probes is particularly useful for identifying polymeric components which are particularly difficult to remove from surfaces in cleaning. For example, multiple probes can detect pectins (such as homogalacturonan, arabinan, galactan, xylogalacturonan moieties), non-cellulosic polymers (such as xylan, mannan, xyloglucan, mixed linkage glucan moieties), proteins including glycoproteins (such as arabinogalactan proteins, hydroxyproline-rich proteins), cellulosic polymers (such as carbohydrate binding modules) and nucleic acids.

The probe is such that a detectable signal is provided when the probe binds to a substrate, enabling detection and optionally providing information about the quantity or relative quantity of the residue-component which is the substrate for that molecular probe. Where the quantitative information is relative it is compared to a second residue-component in the residue or second chemical moiety responding to a different molecular probe and/or the quantity of the residue and/or a residue-component as a result of use of a different cleaning process, composition or component. Standard molecular probe detection techniques are suitable. One preferred detectable signal is provided by a chemical tag conjugated to the molecular probe. For example, the tag may itself provide the detectable change or may confer a change on another detectable substrate, such as a colorimetric or fluorescent change. Any tag allowing detection of the binding partner is contemplated in the invention. Relevant tags comprise all tags commonly employed in molecular probes for example those commonly used in microarrays for detection of genes or expression patterns, immunological assays, enzyme linked immunosorbent assays, fluorescent probes, radiolabels etc. Following contact of the molecular probe with the residue, it may be necessary to contact the molecular probe-residue medium with a secondary antibody which binds to the molecular probe to enable a signal indicating the binding and/or degree of binding of the molecular probe to be detected.

Molecular probes providing a colorimetric response on binding to a substrate or epitope are preferred.

Detection of binding of the probe to a substrate and optional quantification of the substrate may also be accomplished using surface plasmon resonance.

Suitable molecular probes are selected from the group comprising antibodies (including mono- and poly-clonal antibodies), affimers, aptamers, lectins, carbohydrate binding modules and mixtures thereof and are commercially available, or can be designed and made to detect a specific moiety.

The molecular probes may comprise molecular probes for proteins, carbohydrates, nucleotides, nucleic acids, peptides, amino acids, antibiotics, organic or inorganic compounds or ions which may be high (for examples from 900 Daltons) or low molecular weight (for example below 900 Daltons), lipids, small molecules, bacteria and/or viruses. As described above the molecular probes have an affinity to either the specific substrate or an epitope thereof. Preferably in the method of the invention the molecular probes comprise probes for proteins, carbohydrates and/or nucleic acids. Preferably greater than 3, or greater than 4, or greater than 5 or greater than 6, or greater than 7, or greater than 8, or greater than 9, or greater than 10 or greater than 15, or greater than 20, or greater than 25, or greater than 30 or more molecular probes are used, depending on the complexity of the residue to be analysed.

Table 1 provides examples of commercially available probes suitable for use in the present invention.

TABLE 1

| Molecular probe | Specificity | Source |
|---|---|---|
| BAM1-4 | Algal cell wall polysaccharides | SeaProbes |
| BAM6-11 | Alginates | SeaProbes |
| BS-400-2 | Beta-glucan (callose) | Biosupplies |
| BS-400-4 | B-1,4-D-Mannan | Biosupplies |
| CBM27a | B-1,4-D-Mannan | NZYTech |
| DNA-photoproducts(6'-4) | DNA | Absolute antibody |
| Hairpin-DNA | DNA | Absolute antibody |
| JIM1 | Membrane glycoproteins | Kerafast/Megazyme |
| JIM4, 8, 11-16, 20-21 | Proteoglycan | Kerafast/Megazyme |
| JIM5, 7 | Pectic polyaccharide | Kerafast/Megazyme |
| LM1-2, 14, 30 | Proteoglycan | Kerafast/Megazyme |
| LM5-9, 13, 16, 18-20 | Pectic polysaccharide | Kerafast/Megazyme |
| LM10, 27-28 | Xylan | Kerafast/Megazyme |
| LM15, 24-25 | Xyloglucan | Kerafast/Megazyme |
| Z-DNA [Z22] | DNA | Absolute antibody |

The residue may be analysed directly on the soiled or treated surface. For example, where the residue is on the surface of a fabric, the fabric may be contacted directly with the molecular probes. Preferably the residue is extracted from the surface for analysis. The extraction step may comprise liquid extraction, precipitation extraction or physical extraction. The extraction step may comprise one or more of each of the following steps: (i) acid extraction, (ii) base extraction, (iii) chelant extraction (iv) enzyme extraction, (v) salt extraction, (vi) solvent extraction, and/or (vi) physical extraction steps; preferably the extraction step is a multi-step sequential extraction with a combination of two or more of these steps. A preferred multi-step extraction comprises two or more extraction steps selected from: solvent extraction preferably using water as the solvent, chelant extraction, base extraction, salt extraction and enzyme extraction, preferably in that order.

An acid extraction step comprises contacting the surface comprising residue with an aqueous acidic composition and optionally agitating. Any acid can be used, for example ammonium oxalate, acetic acid, citric acid, hydrochloric acid, sulfuric acid, phosphoric acid.

A base extraction step comprises contacting the surface comprising residue with an aqueous alkaline composition and optionally agitating. Any base can be used, for example sodium hydroxide, sodium carbonate. Preferably the aqueous alkaline composition additionally comprises sodium borohydride.

A chelant extraction step comprises contacting the surface comprising residue with an aqueous composition comprising chelant and optionally agitating. Any chelant may be used. Suitable chelants are for example CDTA (trans-1,2-diaminocyclohexane-N,N,N',N'-tetraacetic acid monohydrate or salt thereof), EDTA (ethylenediaminetetraacetic acid or salt thereof), MGDA (methylglycinediacetic acid or salt thereof), GLDA (N,N-Dicarboxymethyl glutamic acid or salt thereof). CDTA and EDTA are particularly preferred.

An enzyme extraction step comprises contacting the surface comprising the residue with an aqueous composition comprising one or more enzymes either together or sequentially.

A salt extraction step comprises contacting the surface comprising the residue with a salt solution, preferably at a high salt concentration such as greater than 2 moles/liter, or greater than 2.5 moles/liter. Any salt can be used, for example sodium chloride and ammonium sulfate.

A preferred solvent extraction comprises contacting the surface comprising residue with deionised water with optional agitation. Other solvents can be used, for example acetone, chloroform, methanol, cadoxen.

In a physical extraction step, a residue is physically removed for example by scraping from the surface. A physical extraction step is particularly preferred for residues from hard surfaces. An aqueous liquor is then prepared by placing the residue in water and optionally agitating.

An extraction step may be chosen to at least partially degrade the surface thereby increasing release of the residue from the surface for analysis. Thus, for example, cellulase enzymes may be particularly preferred, especially when the surface is a cellulosic surface, polyesterase enzymes may be particularly preferred, especially when the residue is on a polyester surface.

In the extraction step the residue is at least partially removed from the surface, producing a residue extract liquor comprising solvent (preferably water but as above, other solvents can be used) and residue components.

The residue extract is then contacted with the molecular probes. Where more than one extraction step is carried out the liquor comprising solvent and residue components from each extraction step may be mixed together and the mixed liquor contacted with the molecular probes; or preferably each of the solvent and residue-containing liquors from the separate extraction steps will be contacted with the molecular probes separately.

The residue may be contacted with the molecular probes by directly mixing a sample of the residue-containing liquor, which is preferably aqueous with a molecular probe in an aqueous medium.

In a preferred method for contacting the residue with the probes, the residue is immobilised/deposited onto a surface in the form of a microarray by printing the residue-containing liquor onto a surface such as a membrane or slide. Suitable surfaces comprise oxidised polystyrene (e.g. MaxiSorp Slides, Willats 2002 (Willats, Rasmussen et al., 2002)), nitrocellulose-coated glass (e.g. Fast Slides, Schleicher & Schuell, Wang 2002 (Wang, Liu et al., 2002)) and nanoporous membranes such as a nitrocellulose membrane.

The deposition or printing can be by any conventional means for preparing a microarray, preferably using a non-contact system, for example ink-jet printing, preferably using a high-throughput printing system. Other non-contact printing techniques include photochemistry-based techniques, laser writing and electrospray deposition. Contact printing technologies can also be used such as pin printing and microstamping. Pin-based systems, where pins are dipped into a solution of the problem soil and then contacted with the immobilised substrate, can also be used. The preferred form of printing is non-contact inkjet piezoelectric printing. The samples are preferably printed side by side on the array, allowing for the simultaneous analysis of many samples.

The microarrays are then analysed by contacting a microarray with each of the molecular probes typically in aqueous solution, with optional agitation for sufficient contact time to allow any binding to take place. If necessary, the microarrays are then placed in a solution and/or undergo the relevant treatment step or steps to provide a visual indication of the degree of binding, depending on the specific probe used. This may involve incubation for example, with a secondary antibody.

The data regarding the molecular probes which have bound to a substrate on contact with a residue-solution and preferably also the information regarding the degree of binding is then analysed. For example, the arrays may be scanned with a flatbed desktop scanner, individually, using greyscale settings and the scanned images interpreted with software e.g. ImaGene or Array-Pro Analyser. Spots can be quantified for example using a semiautomatic grid and transforming the spot data into a colour intensity heatmap in which colour intensity is proportional to the relative level of a residue-component in solution. The binding signals of the probes may be represented by lighter or darker spots, depending on the strength of the binding. A darker spot is indicative of a higher relative amount of a specific epitope or chemical moiety. If the epitope or chemical moiety for a specific molecular probe is not present in the sample, then there is no binding and no spot can be seen. The data from specific molecular probes in the respective residue-solutions from different extraction steps may also be useful.

Using the preferred microarray for contacting the residue with the molecular probes, it is possible to determine the relative abundance of hundreds of chemical moieties, bonds etc, and/or molecules simultaneously, using very small amounts of residue and/or small volumes of residue extracts. The method of the invention provides (i) identification of soils and other residues on fabrics, and even residual soils on fabrics after a cleaning step, (ii) identification of soils and other residues on hard surfaces, including dish-ware, and even residual soils after a cleaning step (iii) identification of soils and other residues on skin, and even residual soils on skin after a cleaning step, (iv) identification of soils and other residues on hair, and even residual soils on hair after a cleaning step; and (v) development of cleaning compositions. The analysis using molecular probes may be combined with other conventional analytical tools.

The invention also provides a method of making a cleaning composition comprising (i) identifying the residue and/or a residue-component as described above, (ii) selecting a first cleaning component capable of promoting removal for example by breakdown or disruption of the residue-component based on the information provided by the response, then (iii) mixing the first cleaning component with a cleaning adjunct.

Depending on the residue-component(s) identified, a first cleaning component is selected and mixed with a cleaning adjunct to make a cleaning composition. The ability of the first cleaning component to promote removal of the residue and/or residue-component may be determined by comparing the presence of and/or amount/relative amount of the residue or residue-component remaining on a surface after a cleaning step with and without the first cleaning component using molecular probes, as described above. Alternatively, on identification of a chemical moiety, bond, motif etc of a residue or residue-component, a first cleaning component may be selected based on the selection of a component or mixture of components that disrupts or breaks such moiety, bond, motif, structure etc. in a conventional way. The efficacy of such selection may be confirmed using the method described herein. For example, if a specific lipid is identified, surfactants or lipase enzymes can be screened to find a suitable first cleaning component for that lipid.

The invention is particularly useful when a residue or residue-component identified is a substrate for an enzyme. An enzyme is then preferably selected as the first component from the class of enzymes suitable for the identified substrate. Enzyme screening may optionally also then be carried out to identify an enzyme from that class of enzymes, or mixture of enzymes which promotes greatest/most effective removal of that residue and/or residue-component. Enzyme screening can be carried out using the method of the invention, comparing the performance/efficacy of alternative enzymes from the class of enzymes. A preferred first cleaning component comprises an enzyme, or enzyme pre-cursor, spore, bacteria or combination thereof.

Enzymes suitable as the first cleaning component include enzymes selected from the group comprising aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannanase, mannosidase, oxidase, pectinolytic enzyme, peptidoglutaminase, peroxidase, phytase, polyphenoloxidase, proteolytic enzyme, ribonuclease, transglutaminase, alginate lyase, xylanase, xanthan lyase, xanthanase, endo-β-1,3-glucanase and mixtures thereof. The enzyme(s) may be produced, for example, by a microorganism belonging to the genus *Aspergillus*, e.g., *Aspergillus aculeatus, Aspergillus awamori, Aspergillus foetidus, Aspergillus fumigatus, Aspergillus japonicus, Aspergillus nidulans, Aspergillus niger*, or *Aspergillus oryzae; Fusarium*, e.g., *Fusarium bactridioides, Fusarium cerealis, Fusarium crookwellense, Fusarium culmorum, Fusarium graminearum, Fusarium graminum, Fusarium heterosporum, Fusarium negundi,*

*Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum; Humicola*, e.g., *Humicola insolens* or *Humicola lanuginosa*; or *Trichoderma*, e.g., *Trichoderma harzianum, Trichoderma koningii, Trichoderma longibrachiatum, Trichoderma reesei*, or *Trichoderma viride*.

Any of the following bacteria, or spores from the following genera may be used as the first cleaning component: *Acetonema, Alkalibacillus, Ammoniphilus, Amphibacillus, Anaerobacter, Anaerospora, Aneurinibacillus, Anoxybacillus, Bacillus, Brevibacillus, Caldanaerobacter, Caloramator, Caminicella, Cerasibacillus, Clostridium, Clostridiisalibacter, Cohnella, Dendrosporobacter, Desulfotomaculum, Desulfosporomusa, Desulfosporosinus, Desulfovirgula, Desulfunispora, Desulfurispora, Filifactor, Filobacillus, Gelria, Geobacillus, Geosporobacter, Gracilibacillus, Halonatronum, Heliobacterium, Heliophilum, Laceyella, Lentibacillus, Lysinibacillus, Mahella, Metabacterium, Moorella, Natroniella, Oceanobacillus, Orenia, Ornithinibacillus, Oxalophagus, Oxobacter, Paenibacillus, Paraliobacillus, Pelospora, Pelotomaculum, Piscibacillus, Planifilum, Pontibacillus, Propionispora, Salinibacillus, Sal suginibacillus, Seinonella, Shimazuella, Sporacetigenium, Sporoanaerobacter, Sporobacter, Sporobacterium, Sporohalobacter, Sporolactobacillus, Sporomusa, Sporosarcina, Sporotalea, Sporotomaculum, Syntrophomonas, Syntrophospora, Tenuibacillus, Tepidibacter, Terribacillus, Thalassobacillus, Thermoacetogenium, Thermoactinomyces, Thermoalkalibacillus, Thermoanaerobacter, Thermoanaeromonas, Thermobacillus, Thermoflavimicrobium, Thermovenabulum, Tuberibacillus, Virgibacillus*, and/or *Vulcanobacillus*.

Preferably, the bacteria that may form spores are from the family *Bacillaceae*, such as species of the genera *Aeribacillus, Aliibacillus, Alkalibacillus, Alkalicoccus, Alkalihalobacillus, Alkalilactibacillus, Allobacillus, Alteribacillus, Alteribacter, Amphibacillus, Anaerobacillus, Anoxybacillus, Aquibacillus, Aquisalibacillus, Aureibacillus, Bacillus, Caldalkalibacillus, Caldibacillus, Calditerricola, Calidifontibacillus, Camelliibacillus, Cerasibacillus, Compostibacillus, Cytobacillus, Desertibacillus, Domibacillus, Ectobacillus, Evansella, Falsibacillus, Ferdinandcohnia, Fermentibacillus, Fictibacillus, Filobacillus, Geobacillus, Geomicrobium, Gottfriedia, Gracilibacillus, Halalkalibacillus, Halobacillus, Halolactibacillus, Heyndrickxia, Hydrogenibacillus, Lederbergia, Lentibacillus, Litchfieldia, Lottiidibacillus, Margalitia, Marinococcus, Melghiribacillus, Mesobacillus, Metabacillus, Microaerobacter, Natribacillus, Natronobacillus, Neobacillus, Niallia, Oceanobacillus, Ornithinibacillus, Parageobacillus, Paraliobacillus, Paralkalibacillus, Paucisalibacillus, Pelagirhabdus, Peribacillus, Piscibacillus, Polygonibacillus, Pontibacillus, Pradoshia, Priestia, Pseudogracilibacillus, Pueribacillus, Radiobacillus, Robertmurraya, Rossellomorea, Saccharococcus, Salibacterium, Salimicrobium, Salinibacillus, Salipaludibacillus, Salirhabdus, Salisediminibacterium, Saliterribacillus, Sal suginibacillus, Sediminibacillus, Siminovitchia, Sinibacillus, Sinobaca, Streptohalobacillus, Sutcliffiella, Swionibacillus, Tenuibacillus, Tepidibacillus, Terribacillus, Terrilactibacillus, Texcoconibacillus, Thalassobacillus, Thalassorhabdus, Thermolongibacillus, Virgibacillus, Viridibacillu, Vulcanibacillus, Weizmannia*. In various examples, the bacteria may be strains of *Bacillus Bacillus acidicola, Bacillus aeolius, Bacillus aerius, Bacillus aerophilus, Bacillus albus, Bacillus altitudinis, Bacillus alveayuensis, Bacillus amyloliquefaciensex, Bacillus anthracis, Bacillus aquiflavi, Bacillus atrophaeus, Bacillus australimaris, Bacillus badius, Bacillus benzoevorans, Bacillus cabrialesii, Bacillus canaveralius, Bacillus capparidis, Bacillus carboniphilus, Bacillus cereus, Bacillus chungangensis, Bacillus coahuilensis, Bacillus cytotoxicus, Bacillus decisifrondis, Bacillus ectoiniformans, Bacillus enclensis, Bacillus fengqiuensis, Bacillus fungorum, Bacillus glycinifermentans, Bacillus gobiensis, Bacillus halotolerans, Bacillus haynesii, Bacillus horti, Bacillus inaquosorum, Bacillus infantis, Bacillus infernus, Bacillus isabeliae, Bacillus kexueae, Bacillus licheniformis, Bacillus luti, Bacillus manusensis, Bacillus marinisedimentorum, Bacillus mesophilus, Bacillus methanolicus, Bacillus mobilis, Bacillus mojavensis, Bacillus mycoides, Bacillus nakamurai, Bacillus ndiopicus, Bacillus nitratireducens, Bacillus oleivorans, Bacillus pacificus, Bacillus pakistanensis, Bacillus paralicheniformis, Bacillus paramycoides, Bacillus paranthracis, Bacillus pervagus, Bacillus piscicola, Bacillus proteolyticus, Bacillus pseudomycoides, Bacillus pumilus, Bacillus safensis, Bacillus salacetis, Bacillus salinus, Bacillus salitolerans, Bacillus seohaeanensis, Bacillus shivajii, Bacillus siamensis, Bacillus smithii, Bacillus solimangrovi, Bacillus songklensis, Bacillus sonorensis, Bacillus spizizenii, Bacillus spongiae, Bacillus stercoris, Bacillus stratosphericus, Bacillus subtilis, Bacillus swezeyi, Bacillus taeanensis, Bacillus tamaricis, Bacillus tequilensis, Bacillus thermocloacae, Bacillus thermotolerans, Bacillus thuringiensis, Bacillus tianshenii, Bacillus toyonensis, Bacillus tropicus, Bacillus vallismortis, Bacillus velezensis, Bacillus wiedmannii, Bacillus wudalianchiensis, Bacillus xiamenensis, Bacillus xiapuensis, Bacillus zhangzhouensis*, or combinations thereof.

In some examples, the bacterial strains that form spores may be strains of *Bacillus*, including: *Bacillus* sp. strain SD-6991; *Bacillus* sp. strain SD-6992; *Bacillus* sp. strain NRRL B-50606; *Bacillus* sp. strain NRRL B-50887; *Bacillus pumilus* strain NRRL B-50016; *Bacillus amyloliquefaciens* strain NRRL B-50017; *Bacillus amyloliquefaciens* strain PTA-7792 (previously classified as *Bacillus atrophaeus*); *Bacillus amyloliquefaciens* strain PTA-7543 (previously classified as *Bacillus atrophaeus*); *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus subtilis* strain PTA-7547; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136 (also known as DA-33R, ATCC accession No. 55406); *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; *Bacillus amyloliquefaciens* strain NRRL B-50607; *Bacillus subtilis* strain NRRL B-50147 (also known as 300R); *Bacillus amyloliquefaciens* strain NRRL B-50150; *Bacillus amyloliquefaciens* strain NRRL B-50154; *Bacillus megaterium* PTA-3142; *Bacillus amyloliquefaciens* strain ATCC accession No. 55405 (also known as 300); *Bacillus amyloliquefaciens* strain ATCC accession No. 55407 (also known as PMX); *Bacillus pumilus* NRRL B-50398 (also known as ATCC 700385, PMX-1, and NRRL B-50255); *Bacillus cereus* ATCC accession No. 700386; *Bacillus thuringiensis* ATCC accession No. 700387 (all of the above strains are available from Novozymes, Inc., USA); *Bacillus*

*amyloliquefaciens* FZB24 (e.g., isolates NRRL B-50304 and NRRL B-50349 TAEGRO® from Novozymes), *Bacillus subtilis* (e.g., isolate NRRL B-21661 in RHAPSODY®, SERENADE® MAX and SERENADE® ASO from Bayer CropScience), *Bacillus pumilus* (e.g., isolate NRRL B-50349 from Bayer CropScience), *Bacillus amyloliquefaciens* TrigoCor (also known as "TrigoCor 1448"; e.g., isolate Embrapa Trigo Accession No. 144/88.4Lev, Cornell Accession No.Pma007BR-97, and ATCC accession No. 202152, from Cornell University, USA) and combinations thereof. Suitable commercially available *Bacillus* spore blends include without limitation Freshen Free™ CAN (10×), available from Novozymes Biologicals, Inc.; Evogen® Renew Plus (10×), available from Genesis Biosciences, Inc.; and Evogen® GT (10×, 20× and 110×), all available from Genesis Biosciences, Inc. In the foregoing list, the parenthetical notations (10×, 20×, and 110×) indicate relative concentrations of the *Bacillus* spores.

The first cleaning component may be selected from the cleaning adjuncts described below. The first cleaning component may be one chemical or a mixture of chemicals. However, as described above, in order to provide the first cleaning component the first cleaning component is selected based on its being capable of promoting removal of the residue and/or residue-component identified based on the response of the molecular probes; or a treatment component is selected based on its being capable of providing effective surface treatment.

A cleaning composition can then be made by mixing the first cleaning component with a cleaning adjunct.

Cleaning adjuncts may be selected from the group comprising surfactants, builders, bleach ingredients, colorants, chelating agents, dye transfer agents, deposition aids, dispersants, enzymes, and enzyme stabilizers, catalytic materials, optical brighteners, photoactivators, fluorescers, fabric hueing agents (shading dyes), fabric conditioners, preformed peracids, polymeric dispersing agents, clay soil removal/anti-redeposition agents, filler salts, hydrotropes, brighteners, suds suppressors, structure elasticizing agents, fabric softeners, preservatives, anti-oxidants, anti-shrinkage agents, germicides, fungicides, anti-tarnish, anti-corrosion agents, alkalinity sources, solubilizing agents, carriers, processing aids, pigments, dyes, perfumes and pH control agents, encapsulates, polymers and mixtures thereof. For example, these may include: bleach ingredients such as bleach activators, bleach boosters such as imine bleach boosters, bleach catalysts, hydrogen peroxide, sources of hydrogen peroxide such as percarbonate and/or perborate, especially percarbonate coated with material such as carbonate and/or sulphate salt, silicate salt, borosilicate, and any mixture thereof, pre-formed peracid, including pre-formed peracid in encapsulated form, transition metal catalysts; suds suppressors or suppressor systems such as silicone based suds suppressors and/or fatty acid based suds suppressors; fabric-softeners such as clay, silicone and/or quaternary ammonium compounds; flocculants such as polyethylene oxide; dye transfer inhibitors such as polyvinylpyrrolidone, poly 4-vinylpyridine N-oxide and/or co-polymer of vinylpyrrolidone and vinylimidazole; fabric integrity components such as oligomers produced by the condensation of imidazole and epichlorhydrin; soil dispersants and soil anti-redeposition aids such as alkoxylated polyamines and ethoxylated ethyleneimine polymers; anti-redeposition components such as polyesters; carboxylate polymers such as maleic acid polymers or co-polymers of maleic and acrylic acid; perfumes such as perfume microcapsules, starch encapsulated accords, perfume spray-on; soap rings; aesthetic particles; aesthetic dyes; fillers such as sodium sulphate and/or citrus fibres, although it may be preferred for the composition to be substantially free of fillers; silicate salt such as sodium silicate, including 1.6R and 2.0R sodium silicate, or sodium metasilicate; co-polyesters of di-carboxylic acids and diols; cellulosic polymers such as methyl cellulose, carboxymethyl cellulose, hydroxyethoxycellulose, or other alkyl or alkylalkoxy cellulose; solvents such as 1,2 propanediol, monoethanolamine; diethylene glycol, ethanol, and any mixture thereof; hydrotropes such as sodium cumene sulphonate, sodium xylene sulphonate, sodium toluene sulphonate, and any mixtures; organic acids and salts thereof, such as citric acid/citrate salts, water; and any combination thereof. Preferably the cleaning adjunct comprises at least one non-water cleaning adjunct. The composition preferably comprises surfactant and optionally one or more cleaning adjunct selected from the group consisting of (i) perfume microcapsule; (ii) fabric hueing agent; (iii) protease; (iv) amylase; (v) lipase; (vi) cellulase; (vii) nuclease; (vii) amphiphilic cleaning polymer; (viii) soil release polymer; or (ix) mixtures thereof.

Preferably the composition comprises a surfactant, typically in an amount from 1 to 60 wt % of the composition. Any surfactant may be suitable, such as anionic, nonionic, cationic, amphoteric or zwitterionic.

Preferred anionic surfactants are sulfonate and sulfate surfactants, preferably alkylbenzene sulphonates and/or (optionally alkoxylated) alkyl sulfates. Particularly preferred anionic surfactant comprises linear alkylbenzene sulfonates (LAS). Preferred alkyl sulfates comprise alkyl ether sulfates, especially C-9-15 alcohol ether sulfates, especially those having an average degree of ethoxylation from 0.5 to 7, preferably from 1 to 5, C8-C16 ester sulfates and C10-C14 ester sulfates, such as mono dodecyl ester sulfates. In a preferred composition the anionic surfactant comprises alkyl benzene sulphonate and optionally in addition, optionally ethoxylated alkyl sulfate, preferably having a degree of ethoxylation from 0 to 7, more preferably from 0.5 to 3. Isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ether sulfates (AES or AEOS or FES, also known as alcohol ethoxy sulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof are also suitable anionic surfactants.

The anionic surfactant is preferably added to the cleaning composition in the form of a salt. Preferred cations are alkali metal ions, such as sodium and potassium. However, the salt form of the anionic surfactant may be formed in situ by neutralization of the acid form of the surfactant with alkali such as sodium hydroxide or an amine, such as mono-, di-, or tri-ethanolamine. The composition preferably comprises from 1 to 60 weight % or from 1 to 50 wt % or 2 or 5 to 40 wt % of the composition, anionic surfactant. The surfactant preferably comprises a surfactant system comprising an anionic surfactant and in addition, one or more additional surfactants, which may be non-ionic including semi-polar and/or cationic and/or zwitterionic and/or ampholytic and/or amphoteric and/or semi-polar nonionic and/or mixtures thereof. A preferred surfactant may comprise an anionic and a nonionic surfactant.

Suitable nonionic surfactants include alcohol ethoxylates (AE), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. Alcohol ethoxylates are particularly preferred, preferably having a C9-18 or preferably a C12-15 alkyl chain and preferably having an average degree of ethoxylation from 3 to 9, more preferably from 3 to 7. Commercially available nonionic surfactants cleaning include Plurafac™, Lutensol™ and Pluronic™ from BASF, Dehypon™ series from Cognis and Genapol™ series from Clariant.

The cleaning composition may comprise from 0.5 wt % to about 40 wt % of a non-ionic surfactant.

Preferably the composition comprises a protease or mixture of more than one protease, a lipase or mixture of more than one lipase, a peroxidase or mixture of more than one peroxidase, one or more amylolytic enzymes, e.g., an alpha-amylase, glucoamylase, maltogenic amylase, and/or a cellulase or mixture thereof.

In general, the properties of the chosen enzyme(s) should be compatible with the selected detergent, (i.e., pH-optimum, compatibility with other enzymatic and non-enzymatic ingredients, etc.), and the enzyme(s) should be present in effective amounts. Preferably, the product of the invention comprises at least 0.01 mg, preferably from about 0.05 to about 10, more preferably from about 0.1 to about 6, especially from about 0.2 to about 5 mg of active further enzyme/g of composition.

Proteases: The composition of the invention preferably comprises a protease. A mixture of two or more proteases can contribute to an enhanced cleaning across a broader temperature, cycle duration, and/or substrate range. Suitable proteases include metalloproteases and serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

- subtilisins (EC 3.4.21.62), especially those derived from *Bacillus*, such as *Bacillus* sp., *B. lentus, B. alkalophilus, B. subtilis, B. amyloliquefaciens, B. pumilus, B. gibsonii*, and *B. akibaii* described in WO2004067737, WO2015091989, WO2015091990, WO2015024739, WO2015143360, U.S. Pat. No. 6,312,936 B1, U.S. Pat. Nos. 5,679,630, 4,760,025, DE102006022216A1, DE102006022224A1, WO2015089447, WO2015089441, WO2016066756, WO2016066757, WO2016069557, WO2016069563, WO2016069569 and WO2016174234. Specifically, mutations S9R, A15T, V66A, A188P, V199I, Q239R, N255D (savinase numbering system).
- trypsin-type or chymotrypsin-type proteases, such as trypsin (e.g., of porcine or bovine origin), including the *Fusarium* protease described in WO 89/06270 and the chymotrypsin proteases derived from Cellumonas described in WO 05/052161 and WO 05/052146.
- metalloproteases, especially those derived from *Bacillus amyloliquefaciens* described in WO07/044993A2; from *Bacillus, Brevibacillus, Thermoactinomyces, Geobacillus, Paenibacillus, Lysinibacillus* or *Streptomyces* spp. Described in WO2014194032, WO2014194054 and WO2014194117; from *Kribella alluminosa* described in WO2015193488; and from *Streptomyces* and *Lysobacter* described in WO2016075078.
- protease having at least 90% identity to the subtilase from *Bacillus* sp. TY145, NCIMB 40339, described in WO92/17577 (Novozymes A/S), including the variants of this *Bacillus* sp TY145 subtilase described in WO2015024739, and WO2016066757.

Especially preferred proteases for the cleaning composition of the invention are polypeptides having at least 90%, preferably at least 95%, more preferably at least 98%, even more preferably at least 99% and especially 100% identity with the wild-type enzyme from *Bacillus lentus*, comprising mutations in one or more, preferably two or more and more preferably three or more of the following positions, using the BPN' numbering system and amino acid abbreviations as illustrated in WO00/37627, which is incorporated herein by reference: S9R, A15T, V68A, N76D, N87S, S99D, S99SD, S99A, S101G, S101M, S103A, V104N/I, G118V, G118R, S128L, P129Q, S130A, Y167A, R170S, A194P, V205I, Q206L/D/E, Y209W, M222S, Q245R and/or M222S.

Most preferably the protease is selected from the group of proteases comprising the below mutations (BPN' numbering system) versus either the PB92 wild-type WO 08/010925) or the subtilisin 309 wild-type (sequence as per PB92 backbone, except comprising a natural variation of N87S).

(i) G118V+S128L+P129Q+S130A
(ii) S101M+G118V+S128L+P129Q+S130A
(iii) N76D+N87R+G118R+S128L+P129Q+S130A+S188D+N248R
(iv) N76D+N87R+G118R+S128L+P129Q+S130A+S188D+V244R
(v) N76D+N87R+G118R+S128L+P129Q+S130A
(vi) V68A+N87S+S101G+V104N
(vii) S99AD
(viii) S9R+A15T+V68A+N218D+Q245R Suitable commercially available protease enzymes include those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase®, Coronase®, Blaze®, Blaze Ultra® and Esperase® by Novozymes A/S (Denmark); those sold under the tradename Maxatase®, Maxacal®, Maxapem®, Properase®, Purafect®, Purafect Prime®, Purafect Ox®, FN3®, FN4®, Excellase®, Ultimase® and Purafect OXP® by Dupont; those sold under the tradename Opticlean® and Optimase® by Solvay Enzymes; and those available from Henkel/Kemira, namely BLAP (sequence shown in FIG. 29 of U.S. Pat. No. 5,352,604 with the following mutations S99D+S101 R+S103A+V104I+G159S, hereinafter referred to as BLAP), BLAP R (BLAP with S3T+V4I+V199M+V205I+L217D), BLAP X (BLAP with S3T+V4I+V205I) and BLAP F49 (BLAP with S3T+

V4I+A194P+V199M+V205I+L217D); and KAP (*Bacillus alkalophilus* subtilisin with mutations A230V+S256G+S259N) from Kao.

Especially preferred for use herein are commercial proteases selected from the group consisting of Properase®, Blaze®, Ultimase®, Everlase®, Savinase®, Excellase®, Blaze Ultra®, BLAP and BLAP variants.

Preferred levels of protease in the product of the invention include from about 0.05 to about 10, more preferably from about 0.5 to about 7 and especially from about 1 to about 6 mg of active protease/g of composition.

Lipases: The composition preferably comprises a lipase. The presence of oils and/or grease can further increase the resiliency of stains comprising mannans and other polysaccharides. As such, the presence of lipase in the enzyme package can further improve the removal of such stains. Suitable lipases include those of bacterial or fungal or synthetic origin. Chemically modified or protein engineered mutants are included. Examples of useful lipases include lipases from *Humicola* (synonym *Thermomyces*), e.g., from *H. lanuginosa* (*T. lanuginosus*) or from *H. insolens*, a *Pseudomonas* lipase, e.g., from *P. alcaligenes* or *P. pseudoalcaligenes, P. cepacia P. stutzeri, P. fluorescens, Pseudomonas* sp. strain SD 705, *P. wisconsinensis*, a *Bacillus* lipase, e.g., from *B. subtilis* (Dartois et al. (1993), Biochemica et Biophysica Acta, 1131, 253-360), *B. stearothermophilus* or *B. pumilus.*

The lipase may be a "first cycle lipase" such as those described in U.S. Pat. No. 6,939,702 B1 and US PA 2009/0217464. In one aspect, the lipase is a first-wash lipase, preferably a variant of the wild-type lipase from *Thermomyces lanuginosus* comprising T231R and N233R mutations. The wild-type sequence is the 269 amino acids (amino acids 23-291) of the Swissprot accession number Swiss-Prot O59952 (derived from *Thermomyces lanuginosus* (*Humicola lanuginosa*)). Preferred lipases include those sold under the tradenames Lipex®, Lipolex® and Lipoclean®.

Other suitable lipases include: Liprl 139, e.g. as described in WO2013/171241; TfuLip2, e.g. as described in WO2011/084412 and WO2013/033318; *Pseudomonas stutzeri* lipase, e.g. as described in WO2018228880; *Microbulbifer thermotolerans* lipase, e.g. as described in WO2018228881; *Sulfobacillus acidocaldarius* lipase, e.g. as described in EP3299457; LIP062 lipase e.g. as described in WO2018209026; PinLip lipase e.g. as described in WO2017036901 and *Absidia* sp. lipase e.g. as described in WO2017005798.

Suitable lipases are commercially available from Novozymes, for example as Lipex Evity 100L, Lipex Evity 200L (both liquid raw materials) and Lipex Evity 105T (a granulate). These lipases have different structures to the products Lipex 100L, Lipex 100T and Lipex Evity 100T which are outside the scope of the invention.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum*. disclosed in U.S. Pat. Nos. 4,435,307, 5,648,263, 5,691,178, 5,776,757 and 5,691,178.

Suitable endoglucanases are sold under the tradenames Celluclean® and Whitezyme® (Novozymes A/S, Bagsvaerd, Denmark). Examples include Celluclean® 5000L, Celluclean® Classic 400L, Celluclean® Classic 700T, Celluclean® 4500T, Whitezyme® 1.5T, Whitezyme® 2.0L.

Other commercially available cellulases include Celluzyme®, Carezyme®, Carezyme® Premium (Novozymes A/S), Clazinase®, Puradax HA®, Revitalenz® 1000, Revitalenz® 2000 (Genencor International Inc.), KAC-500(B)® (Kao Corporation), Biotouch® FCL, Biotouch® DCL, Biotouch® DCC, Biotouch® NCD, Biotouch® FCC, Biotouch® FLX1 (AB Enzymes)

Suitable glucanases include endo-β-1,3-glucanases, preferably from E.C. class 3.2.1.39, preferably obtained from *Paenibacillus* sp, *Zobellia galactanivorans, Thermotoga petrophila* or *Trichoderma* sp micro-organism, preferably *Paenibacillus* sp or *Zobellia galactanivorans*, most preferably *Paenibacillus* sp.

Amylases. Preferably the composition of the invention may comprise an amylase. Suitable alpha-amylases include those of bacterial or fungal origin. Chemically or genetically modified mutants (variants) are included. A preferred alkaline alpha-amylase is derived from a strain of *Bacillus*, such as *Bacillus licheniformis, Bacillus amyloliquefaciens, Bacillus stearothermophilus, Bacillus subtilis*, or other *Bacillus* sp., such as *Bacillus* sp. NCBI 12289, NCBI 12512, NCBI 12513, DSM 9375 (U.S. Pat. No. 7,153,818) DSM 12368, DSMZ no. 12649, KSM AP1378 (WO 97/00324), KSM K36 or KSM K38 (EP 1,022,334). Preferred amylases include:

(a) variants described in U.S. Pat. No. 5,856,164 and WO99/23211, WO 96/23873, WO00/60060, WO06/002643 and WO2017/192657.
(b) variants described in WO2011/100410 and WO2013/003659.
(c) variants in U.S. Pat. No. 6,093,562.
(d) variants described in WO 09/149130,
(e) variants described in WO10/115021.
(f) variants in WO2016091688.
(g) variants described in WO2014099523.
(h) variants described in WO2014099523.
(i) variants in WO2009149271.
(j) variants described in WO2016180748.
(k) variants described in WO2018060216.

Preferred amylases are engineered enzymes, wherein one or more of the amino acids prone to bleach oxidation have been substituted by an amino acid less prone to oxidation. In particular it is preferred that methionine residues are substituted with any other amino acid. In particular it is preferred that the methionine most prone to oxidation is substituted.

Suitable commercially available alpha-amylases include DURAMYL®, LIQUEZYME®, TERMAMYL®, TERMAMYL ULTRA®, NATALASE®, SUPRAMYL®, STAINZYME®, STAINZYME PLUS®, FUNGAMYL®, ATLANTIC®, ACHIEVE ALPHA®, AMPLIFY® PRIME, INTENSA® and BAN® (Novozymes A/S, Bagsvaerd, Denmark), KEMZYM® AT 9000 Biozym Biotech Trading GmbH Wehlistrasse 27b A-1200 Wien Austria, RAPIDASE®, PURASTAR®, ENZYSIZE®, OPTISIZE HT PLUS®, POWERASE®, PREFERENZ S® series (including PREFERENZ S1000® and PREFERENZ 52000® and PURASTAR OXAM® (DuPont, Palo Alto, California) and KAM® (Kao, 14-10 Nihonbashi Kayabacho, 1-chome, Chuo-ku Tokyo 103-8210, Japan).

Preferably, the composition comprises at least 0.01 mg, preferably from about 0.05 to about 10, more preferably from about 0.1 to about 6, especially from about 0.2 to about 5 mg of active amylase/g of composition.

Peroxidases/Oxidases: Suitable peroxidases/oxidases include those of plant, bacterial or fungal origin. Chemically modified or protein engineered mutants are included.

Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME® (Novozymes A/S).

Pectate lyase: Suitable pectate lyases include those sold under the tradenames Pectawash®, Pectaway®, X-Pect®, (all Novozymes A/S, Bagsvaerd, Denmark) Preferenz® F1000 (DuPont Industrial Biosciences).

Mannanases. The composition preferably comprises one of more mannanase enzymes. As used herein, the term "mannanase" or "galactomannanase" denotes a mannanase enzyme defined according to that known in the art as mannan endo-1,4-beta-mannosidase and having the alternative names beta-mannanase and endo-1,4-mannanase and catalysing hydrolysis of 1,4-beta-D-mannosidic linkages in mannans, galactomannans, glucomannans, and galactoglucomannans. Mannanases are classified according to the Enzyme Nomenclature as EC 3.2.1.78 and belong in Glycosyl Hydrolase families 5, 26 and 113. Many suitable mannanases belong to Glycosyl Hydrolase family 5. Commercially available mannanases include all those sold under the tradenames Mannaway® (Novozymes A/S) such as Mannaway® 200L and Mannaway Evity 4.0T Other commercially available mannanases include Effectenz® M1000, Mannastar® 375, Preferenz M100 and Purabrite® (all DuPont Industrial Biosciences) and Biotouch M7 (AB Enzymes). Other suitable mannanases belong to Glycosyl Hydrolase family 26 including those described in WO2018191135, WO2015040159, WO2017021515, WO2017021516, WO2017021517 and WO2019081515. Suitable mixtures of mannanases include the combinations of Glycosyl Hydrolase family 5 and Glycosyl Hydrolase family 26 mannanases described in WO2019081515.

Xanthan gum-degrading enzymes: The composition may comprise one of more xanthan gum-degrading enzymes. Suitable enzymes for degradation of xanthan gum-based soils include xanthan endoglucanase, optionally in conjunction with a xanthan lyase. As used herein, the term "xanthan endoglucanase" denotes an enzyme exhibiting endo-β-1,4-glucanase activity that is capable of catalysing hydrolysis of the 1,4-linked β-D-glucose polymeric backbone of xanthan gum, optionally in conjunction with a suitable xanthan lyase enzyme. Suitable xanthan endoglucanases are described in WO2013167581, WO2015181299, WO2015181292, WO2017046232, WO2017046260, WO201837062, WO201837065, WO2019038059 and WO2019162000. As used herein, the term "xanthan lyase" denotes an enzyme that cleaves the β-D-mannosyl-β-D-1,4-glucuronosyl bond of xanthan gum. Such enzymes belong to E.C. 4.2.2.12. Suitable xanthan lyases are described in WO2015001017, WO2018037061, WO201837064, WO2019038060, WO2019162000 and WO2019038057.

Nucleases: Preferably the composition comprises a nuclease such as a RNase or DNase or mixtures thereof. The nuclease enzyme is an enzyme capable of cleaving the phosphodiester bonds between the nucleotide sub-units of nucleic acids. The nuclease enzyme herein is preferably a deoxyribonuclease or ribonuclease enzyme or a functional fragment thereof. By functional fragment or part is meant the portion of the nuclease enzyme that catalyzes the cleavage of phosphodiester linkages in the DNA backbone and so is a region of said nuclease protein that retains catalytic activity. Thus it includes truncated, but functional versions, of the enzyme and/or variants and/or derivatives and/or homologues whose functionality is maintained.

Preferably the nuclease enzyme is a deoxyribonuclease, preferably selected from any of the classes E.C. 3.1.21.x, where x=1, 2, 3, 4, 5, 6, 7, 8 or 9, E.C. 3.1.22.y where y=1, 2, 4 or 5, E.C. 3.1.30.z where z=1 or 2, E.C. 3.1.31.1 and mixtures thereof.

DNase: Suitable DNases include wild-types and variants of DNases defined in WO2017162836 (Novozymes), and variants of the *Bacillus cibi* DNase including those described in WO2018011277 (Novozymes), incorporated herein by reference. Preferred DNases are as claimed in co-pending European Patent Application No. EP18202967.

RNase: suitable RNases include wild-types and variants of DNases defined in WO2018178061 (Novozymes), incorporated herein by reference.

Hexosaminidases: The composition may comprise one or more hexosaminidases. The term hexosaminidase includes "dispersin" and the abbreviation "Dsp", which means a polypeptide having hexosaminidase activity, EC 3.2.1.- that catalyzes the hydrolysis of β-1,6-glycosidic linkages of N-acetyl-glucosamine polymers found in soils of microbial origin. The term hexosaminidase includes polypeptides having N-acetylglucosaminidase activity and β-N-acetylglucosaminidase activity. Hexosaminidase activity may be determined according to Assay II described in WO2018184873. Suitable hexosaminidases include those disclosed in WO2017186936, WO2017186937, WO2017186943, WO2017207770, WO2018184873, WO2019086520, WO2019086528, WO2019086530, WO2019086532, WO2019086521, WO2019086526, WO2020002604, WO2020002608, WO2020007863, WO2020007875, WO2020008024, WO2020070063, WO2020070249, WO2020088957, WO2020088958 and WO2020207944. Variants of the *Terribacillus saccharophilus* hexosaminidase defined in WO2020207944 may be preferred, especially the variants with improved thermostability disclosed in that publication.

Galactanase: Preferably the composition comprises a galactanase, ie. an extracellular polymer-degrading enzyme that includes an endo-beta-1,6-galactanase enzyme. The term "endo-beta-1,6-galactanase" or "a polypeptide having endo-beta-1,6-galactanase activity" means a endo-beta-1,6-galactanase activity (EC 3.2.1.164) from the glycoside hydrolase family 30 that catalyzes the hydrolytic cleavage of 1,6-3-D-galactooligosaccharides with a degree of polymerization (DP) higher than 3, and their acidic derivatives with 4-O-methylglucosyluronate or glucosyluronate groups at the non-reducing terminals. For purposes of the present disclosure, endo-beta-1,6-galactanase activity is determined according to the procedure described in WO 2015185689 in Assay I. Suitable examples from class EC 3.2.1.164 are described in WO 2015185689. Any enzyme(s) may be included in the cleaning composition by adding separate enzyme additives containing an enzyme, or a combined enzyme additive comprising two or several or all of the enzymes present in the composition. Such an enzyme additive can be in the form of a granulate, a liquid or slurry, preferably additionally comprising an enzyme stabiliser.

Preferably each enzyme will be present in the composition in an amount of at least 0.0001 to about 0.1% weight percent of pure active enzyme protein, such as from about 0.0001% to about 0.01%, from about 0.001% to about 0.01% or from about 0.001% to about 0.01% based on the weight of the composition.

Fabric Hueing Agent. The composition may comprise a fabric hueing agent (sometimes referred to as shading, bluing or whitening agents/dyes). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof. Preferred are azo dyes, especially mono- or bis- azo dyes, triarylmethane dyes and anthraquinone dyes.

Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Colour Index (C.I.) classifications of Direct, Basic, Reactive or hydrolysed Reactive, Solvent or Disperse dyes. Examples of suitable small molecule dyes include for example small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49, 50 and 51, Acid Blue dyes such as 15, 17, 25, 29, 40, 45, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes such as those described in EP1794275 or EP1794276, or dyes as disclosed in U.S. Pat. No. 7,208,459 B2, and mixtures thereof.

Preferred are polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Polymeric dyes include those described in WO2011/98355, WO2011/47987, US2012/090102, WO2010/145887, WO2006/055787 and WO2010/142503.

Preferred polymeric dyes comprise alkoxylated, preferably ethoxylated azo, anthraquinone or triarylmethane dyes. Ethoxylated thiophene azo dyes are especially preferred, for example polymeric dyes selected from the group consisting of fabric-substantive colorants sold under the name of Liquitint® (Milliken, Spartanburg, South Carolina, USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. Suitable polymeric dyes include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenylmethane polymeric colourants, alkoxylated thiophene polymeric colourants, and mixtures thereof.

Preferred hueing dyes include the alkoxylated thiophene azo whitening agents found in US2008/0177090 which may be optionally anionic, such as those selected from Examples 1-42 in Table 5 of WO2011/011799. Other preferred dyes are disclosed in U.S. Pat. No. 8,138,222.

Suitable pigments include pigments selected from the group consisting of Ultramarine Blue (C.I. Pigment Blue 29), Ultramarine Violet (C.I. Pigment Violet 15) and mixtures thereof. Pigments and/or dyes may also be added to add colour for aesthetic reasons. Preferred are organic blue, violet and/or green pigments.

Builders: The cleaning composition may further contain builders, such as builders based on carbonate, bicarbonate or silicates which may be Zeolites, such as Zeolite A, Zeolite MAP (Maximum Aluminium type P). Zeolites, useable in laundry preferably has the formula Na12(AlO2)12(SiO2) 12·27H2O and the particle size is usually between 1-10 μm for zeolite A and 0.7-2 um for zeolite MAP. Other builders are Sodium metasilicate (Na2SiO3·nH2O or Na2Si2O5·nH2O) strong alkaline and preferably used in dish wash. In preferred embodiments, the amount of a detergent builder may be above 5%, above 10%, above 20%, above 30%, above 40% or above 50%, and may be below 80%, 65%. In a dishwash detergent, the level of builder is typically 40-65%, particularly 50-65% or even 75-90%.

Encapsulates: The composition may comprise an encapsulated benefit agent, comprising a core and a shell having an inner and outer surface, said shell encapsulating said core. The core may comprise a material selected from the group consisting of perfumes; brighteners; dyes; insect repellants; silicones; waxes; flavors; vitamins; fabric softening agents; skin care agents in one aspect, paraffins; enzymes; anti-bacterial agents; bleaches; sensates; and mixtures thereof. The shell may comprise a material selected from the group consisting of polyethylenes; polyamides; polystyrenes; polyisoprenes; polycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect said polysaccharide may comprise alginate and/or chitosan; gelatin; shellac; epoxy resins; vinyl polymers; water insoluble inorganics; silicone; and mixtures thereof. Preferred encapsulates comprise a core comprising perfume. Such encapsulates are perfume microcapsules.

Enzyme stabilizer: The composition may comprise an enzyme stabilizer. Suitable enzyme stabilisers may be selected from the group consisting of (a) inorganic salts selected from the group consisting of calcium salts, magnesium salts and mixtures thereof; (b) carbohydrates selected from the group consisting of oligosaccharides, polysaccharides and mixtures thereof and sugar or sugar alcohol; (c) mass efficient reversible protease inhibitors selected from the group consisting of phenyl boronic acid and derivatives thereof, e.g., an aromatic borate ester, or a phenyl boronic acid derivative such as 4-formylphenyl boronic acid, or a peptide aldehyde such as di-, tri- or tetrapeptide aldehydes or aldehyde analogues (either of the form B1-B0-R wherein, R is H, CH3, CX3, CHX2, or CH2X (X=halogen), B0 is a single amino acid residue (preferably with an optionally substituted aliphatic or aromatic side chain); and B1 consists of one or more amino acid residues (preferably one, two or three), optionally comprising an N-terminal protection group, or as described in WO09118375, WO98/13459); and (d) reversible protease inhibitors such as a boron containing compound; (e) polyols such as propylene glycol or glycerol 1-2 propane diol; (f) calcium formate and/or sodium formate; (g) protease inhibitor of the protein type such as RASI, BASI, WASI (bifunctional alpha-amylase/subtilisin inhibitors of rice, barley and wheat) or CI2 or SSI and (h) any combination thereof.

Structurant: In one aspect, the composition may comprise a structurant selected from the group consisting of diglycerides and triglycerides, ethylene glycol distearate microcrystalline cellulose, cellulose-based materials, microfiber cellulose, biopolymers, xanthan gum, gellan gum, and mixtures thereof.

Polymers: The composition preferably comprises one or more polymers. Preferred examples are carboxymethylcellulose, poly(vinyl-pyrrolidone), poly (ethylene glycol), poly (vinyl alcohol), poly(vinylpyridine-N-oxide), poly(vinylimidazole), polycarboxylates such as polyacrylates, maleic/acrylic acid copolymers and lauryl methacrylate/acrylic acid co-polymers and amphiphilic polymers and mixtures thereof.

Amphiphilic cleaning polymers: Preferably, the amphiphilic cleaning polymer is a compound having the following general structure: bis((C2H5O)(C2H4O)n)(CH3)—N+—CxH2x-N+—(CH3)-bis((C2H5O)(C2H4O)n), wherein n=from 20 to 30, and x=from 3 to 8, or sulphated or sulphonated variants thereof.

Amphiphilic alkoxylated grease cleaning polymers of the present invention refer to any alkoxylated polymer having balanced hydrophilic and hydrophobic properties such that they remove grease particles from fabrics and surfaces. Specific embodiments of the amphiphilic alkoxylated grease cleaning polymers of the present invention comprise a core structure and a plurality of alkoxylate groups attached to that core structure. These may comprise alkoxylated polyalkylenimines, preferably having an inner polyethylene oxide block and an outer polypropylene oxide block.

The core structure may comprise a polyalkylenimine structure comprising, in condensed form, repeating units of formulae (I), (II), (III) and (IV):

(I)

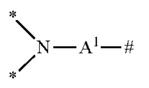

(II)

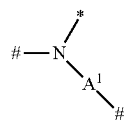

(III)

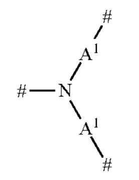

(IV)

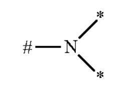

wherein # in each case denotes one-half of a bond between a nitrogen atom and the free binding position of a group A1 of two adjacent repeating units of formulae (I), (II), (III) or (IV); * in each case denotes one-half of a bond to one of the alkoxylate groups; and A1 is independently selected from linear or branched C2-C6-alkylene; wherein the polyalkylenimine structure consists of 1 repeating unit of formula (I), x repeating units of formula (II), y repeating units of formula (III) and y+1 repeating units of formula (IV), wherein x and y in each case have a value in the range of from 0 to about 150; where the average weight average molecular weight, Mw, of the polyalkylenimine core structure is a value in the range of from about 60 to about 10,000 g/mol.

The core structure may alternatively comprise a polyalkanolamine structure of the condensation products of at least one compound selected from N-(hydroxyalkyl)amines of formulae (I.a) and/or (I.b), (I.a)

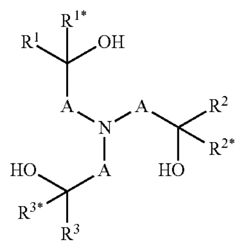

(I.b)

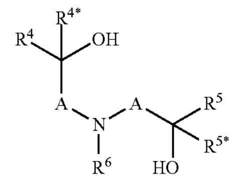

wherein A are independently selected from C1-C6-alkylene; R1, R1*, R2, R2*, R3, R3*, R4, R4*, R5 and R5* are independently selected from hydrogen, alkyl, cycloalkyl or aryl, wherein the last three mentioned radicals may be optionally substituted; and R6 is selected from hydrogen, alkyl, cycloalkyl or aryl, wherein the last three mentioned radicals may be optionally substituted.

The plurality of alkylenoxy groups attached to the core structure are independently selected from alkylenoxy units of the formula (V)

(V)

wherein * in each case denotes one-half of a bond to the nitrogen atom of the repeating unit of formula (I), (II) or (IV); A2 is in each case independently selected from 1,2-propylene, 1,2-butylene and 1,2-isobutylene; A3 is 1,2-propylene; R is in each case independently selected from hydrogen and C1-C4-alkyl; m has an average value in the range of from 0 to about 2; n has an average value in the range of from about 20 to about 50; and p has an average value in the range of from about 10 to about 50.

Carboxylate polymer: The composition preferably also includes one or more carboxylate polymers such as a maleate/acrylate random copolymer or polyacrylate homopolymer. In one aspect, the carboxylate polymer is a polyacrylate homopolymer having a molecular weight of from 4,000 Da to 9,000 Da, or from 6,000 Da to 9,000 Da.

Soil release polymer: The composition preferably also comprises one or more soil release polymers having a structure as defined by one of the following structures (I), (II) or (III):

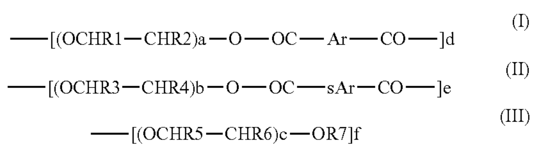

(I)

(II)

(III)

wherein:

a, b and c are from 1 to 200;

d, e and f are from 1 to 50;

Ar is a 1,4-substituted phenylene;

sAr is 1,3-substituted phenylene substituted in position 5 with SO3Me;

Me is Li, K, Mg/2, Ca/2, Al/3, ammonium, mono-, di-, tri-, or tetraalkylammonium wherein the alkyl groups are C1-C18 alkyl or C2-C10 hydroxyalkyl, or mixtures thereof;

R1, R2, R3, R4, R5 and R6 are independently selected from H or C1-C18 n- or iso-alkyl; and R7 is a linear or branched C1-C18 alkyl, or a linear or branched C2-C30 alkenyl, or a cycloalkyl group with 5 to 9 carbon atoms, or a C8-C30 aryl group, or a C6-C30 arylalkyl group.

Suitable soil release polymers are polyester soil release polymers such as Repel-o-tex polymers, including Repel-o-tex SF, SF-2 and SRP6 supplied by Rhodia. Other suitable soil release polymers include Texcare polymers, including Texcare SRA100, SRA300, SRN100, SRN170, SRN240, SRN300 and SRN325 supplied by Clariant. Other suitable soil release polymers are Marloquest polymers, such as Marloquest SL supplied by Sasol.

Cellulosic polymer: The composition preferably also comprises one or more cellulosic polymers including those selected from alkyl cellulose, alkyl alkoxyalkyl cellulose, carboxyalkyl cellulose, alkyl carboxyalkyl cellulose. In one aspect, the cellulosic polymers are selected from the group comprising carboxymethyl cellulose, methyl cellulose, methyl hydroxyethyl cellulose, methyl carboxymethyl cellulose, and mixtures thereof. In one aspect, the carboxymethyl cellulose has a degree of carboxymethyl substitution from 0.5 to 0.9 and a molecular weight from 100,000 Da to 300,000 Da.

Bleaching system: The composition may contain a bleaching system, for example comprising a H2O2 source such as perborate or percarbonate which may be combined with a peracid-forming bleach activator such as tetraacetylethylenediamine or nonanoyloxybenzenesulfonate. Alternatively, the bleaching system may comprise peroxyacids of, e.g., the amide, imide, or sulfone type. In general, when a bleaching agent is used, the compositions of the present invention may comprise from about 0.1% to about 30% or even from about 0.1% to about 25% bleaching agent by weight of the subject cleaning composition.

Chelating Agents: The composition preferably comprises a chelating agent, preferably in an amount from 0.005% to about 15% or even from about 3.0% to about 10% chelating agent by weight of the composition. Suitable chelating agents include copper, iron and/or manganese chelating agents and mixtures thereof. Preferred chelants (complexing agents) include DTPA (Diethylene triamine pentaacetic acid), HEDP (Hydroxyethane diphosphonic acid), DTPMP (Diethylene triamine penta(methylene phosphonic acid)), 1,2-Dihydroxybenzene-3,5-disulfonic acid disodium salt hydrate, ethylenediamine, diethylene triamine, ethylenediaminedisuccinic acid (EDDS), N-hydroxy ethyl ethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), methyl-glycine-diacetic acid (MGDA), glutamic-N,N-diacetic acid (GLDA), iminodisuccinic acid (IDS), carboxy methyl inulin; and salts derivatives thereof and mixtures thereof. Preferred chelants are selected from the group consisting of methyl-glycine-diacetic acid (MGDA), its salts and derivatives thereof, glutamic-N,N-diacetic acid (GLDA), its salts and derivatives thereof, iminodisuccinic acid (IDS), its salts and derivatives thereof, carboxy methyl inulin, its salts and derivatives thereof and mixtures thereof. MGDA and salts thereof are especially preferred, in particular comprising the three-sodium salt of MGDA.

The composition may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, organic solvents such as ethanol or perfumes.

The cleaning composition may be in the form of a composition for use in a main wash step or as pre-treatment or rinse-added cleaning composition for consumer or institutional use.

Typically, the cleaning adjunct will comprise a mixture comprising more than one of the cleaning adjunct materials above and in an amount such that the amount of the first cleaning component and the amount of cleaning adjuncts creates the total cleaning composition.

EXAMPLES

Example 1

Comprehensive Microarray Polymer Profiling of Soiled and Unsoiled Cotton Fabric

Soil residues were extracted from soiled and unsoiled cotton fabrics with 4 different extraction steps: aqueous extraction, chelant extraction, alkaline extraction, high salt extraction steps, in that order.

The same fabric weight to extractant ratio was used for all samples. Extraction steps required samples to be incubated, sequentially, with the respective extractant for 1-2 hours, together with 4-5 borosilicate glass beads and subjected to physical agitation. Soil-residue containing supernatants were obtained by centrifugation.

These supernatant extracts were printed onto nitrocellulose microarrays, probed with molecular probes of interest and analyzed as described in Vidal-Melgosa et al., 2015 (PMID 25657012)

A list of molecular probes used for this screen is given in table 1 above.

Analysis of these samples through three independent repeats showed similar substrate profiles each time. In the analysed samples mannan residues were detected in the soiled cotton sample that were not present in the unsoiled cotton. A detergent composition for improved stain removal is then prepared by adding a mannanase enzyme to a detergent composition, providing improved soil removal.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of identifying a residue and/or residue-component in a residue on a surface, comprising:
- (i) in a first step, contacting the residue with at least five molecular probes wherein:
  - a. a first molecular probe of a probe class selected from the group comprising antibodies, affimers, aptamers, lectins, and carbohydrate binding modules; and
  - b. wherein a second molecular probe and/or a third molecular probe are each of a probe class selected from the group comprising antibodies, affimers, aptamers, lectins, and carbohydrate binding modules, with the proviso that the class of the second and third molecular probes are different from the probe class of the first molecular probe, wherein the second and third classes being the same as or different from one another, and mixtures thereof;
- (ii) in a second step, detecting a positive response from one or more probes, the collective response from said at least five molecular probes providing information regarding the identity, and optionally quantity, of the residue and/or residue-component in the residue.

2. A method according to claim 1 wherein the residue comprises soil.

3. A method according to claim 1 wherein the surface is a support surface and the residue and/or residue component is an extract from a soiled surface.

4. A method according to claim 3 wherein the molecular probes comprise molecular probes providing a colorimetric response on binding.

5. A method according to claim 3 wherein the support surface is a charged surface.

6. A method according to claim 3 wherein the support surface is in the form of a micro-array.

7. A method according to claim 1 comprising additionally quantifying the residue and/or residue-component.

8. A method of making a cleaning composition comprising:
- (i) in a first step, contacting a residue and/or residue component in a residue on a surface with at least five molecular probes, wherein:
  - a. the first molecular probe of a probe class selected from the group comprising antibodies, affimers, aptamers, lectins, carbohydrate binding modules, and
  - b. a second and/or a third molecular probes is selected from the group comprising antibodies, affimers, aptamers, lectins, and carbohydrate binding modules, with the proviso that the class of the second and third molecular probes are different from the probe class of the first molecular probe, wherein the second and third classes being the same as or different from one another, and mixtures thereof;
- (ii) in a second step, detecting a positive response from one or more probes, the collective response from said at least five molecular probes providing information regarding the identity of the residue and/or residue-component in the residue, to provide an identified residue and/or identified residue-component; and
- (iii) selecting a first cleaning component capable of promoting removal of the identified residue and/or identified residue-component; and
- (iv) mixing the first cleaning component with a cleaning adjunct to form a cleaning composition.

9. A method according to claim 8 wherein the surface is a support surface and the residue and/or residue component is an extract from a soiled surface.

10. A method according to claim 9 wherein the support surface is in the form of a micro-array.

11. A method according to claim 9 wherein the support surface is a charged surface.

12. A method according to claim 9 wherein an identified residue or residue-component is a substrate for an enzyme and the first cleaning component comprises an enzyme or enzyme-precursor for said substrate.

13. A method of determining relative performance, and optionally improving a cleaning process or cleaning composition, comprising:
- (i) cleaning a soiled surface in a first cleaning process, said first cleaning process having one or more cleaning conditions selected from the list comprising: wash time, temperature, number or sequence of wash steps, wash water volume and/or other physical conditions and/or cleaning composition and/or concentration thereof, and/or order of addition of cleaning composition components in pre-wash, wash and/or rinse steps, to provide a cleaned surface;
- (ii) identifying a residue and/or residue-component remaining on the cleaned surface according to claim 1,
- (iii) optionally quantifying such residue and/or residue component;
- (iv) changing one or more cleaning conditions, to provide a second cleaning process;
- (v) cleaning the soiled surface in said second cleaning process
- (vi) identifying the residue and/or residue-component remaining on the cleaned surface according to claim 1;
- (vii) optionally quantifying such residue and/or residue component after said second cleaning process;
- (viii) comparing the residue and/or residue component and optionally quantity thereof, remaining after said first cleaning process and said second cleaning process to determine the relative performance of said first cleaning process and/or cleaning composition used therein, and said second cleaning process and/or cleaning composition used therein.

14. A method according to claim 13 wherein the surface is a support surface and the residue and/or residue component is an extract from a soiled surface.

15. A method according to claim 14 wherein the support surface is a charged surface.

16. A method according to claim 14 wherein the support surface is in the form of a micro-array.

17. A method according to claim 13 wherein the molecular probes comprise molecular probes providing a colorimetric response on binding.

18. A method of determining relative performance or improving a surface treatment composition and/or process comprising depositing a surface treatment component onto a surface, the method comprising:

(i) treating a surface in a first surface treatment process having one or more treatment conditions selected from: temperature, number or sequence of treatment steps, number or sequence of wash and/or rinse steps, wash and/or rinse water volume and/or other physical conditions, and/or surface treatment composition and concentration thereof, and/or surface treatment component order of addition in pre-wash, wash and/or rinse steps, (ii) identifying and/or quantifying a residue and/or residue-component which is a surface treatment component remaining on the surface, according to claim 1, (iii) changing at least one of the treatment conditions to provide a second surface treatment process, (iv) treating the surface with the second treatment process, (v) identifying and/or quantifying the residue and/or residue-component after the second surface treatment process, (vi) comparing the residue and/or residue component and optionally quantity thereof, remaining after said first treatment process and said second treatment process to determine the relative performance of the first treatment process and the second treatment process.

19. A method according to claim 18 wherein the molecular probes comprise molecular probes providing a colorimetric response on binding.

20. A method according to claim 18 wherein the support surface is in the form of a micro-array.

* * * * *